US 011142461 B2

(12) United States Patent
Koo

(10) Patent No.: US 11,142,461 B2
(45) Date of Patent: Oct. 12, 2021

(54) METHOD FOR RECYCLING CARBON DIOXIDE

(71) Applicant: SK Innovation Co., Ltd., Seoul (KR)

(72) Inventor: Min Su Koo, Daejeon (KR)

(73) Assignee: SK Innovation Co., Ltd., Seoul (KR)

(*) Notice: Subject to any disclaimer, the term of this patent is extended or adjusted under 35 U.S.C. 154(b) by 0 days.

(21) Appl. No.: 16/842,210

(22) Filed: Apr. 7, 2020

(65) Prior Publication Data
US 2020/0325026 A1 Oct. 15, 2020

(30) Foreign Application Priority Data

Apr. 10, 2019 (KR) .................. 10-2019-0041781

(51) Int. Cl.
| | |
|---|---|
| C10G 2/00 | (2006.01) |
| C07C 1/04 | (2006.01) |
| C07C 29/15 | (2006.01) |
| C01B 32/40 | (2017.01) |
| C01B 13/18 | (2006.01) |
| C01B 13/20 | (2006.01) |

(Continued)

(52) U.S. Cl.
CPC ............... *C01B 32/40* (2017.08); *B01J 19/28* (2013.01); *C01B 13/18* (2013.01); *C01B 13/20* (2013.01); *C01B 13/324* (2013.01); *C07C 1/041* (2013.01); *C07C 29/151* (2013.01); *C07C 41/01* (2013.01); *C10G 2/30* (2013.01); *F27B 7/10* (2013.01); *F27B 7/20* (2013.01); *B01J 2219/187* (2013.01); *B01J 2219/1943* (2013.01); *B01J 2219/3322* (2013.01); *B01J 2219/3325* (2013.01); *C01B 2203/02* (2013.01); *C01B 2203/0222* (2013.01)

(58) Field of Classification Search
None
See application file for complete search history.

(56) References Cited

U.S. PATENT DOCUMENTS 4,622,308 A * 11/1986 Koikeda ................ B01J 29/061
423/326
5,897,686 A * 4/1999 Golden ................ B01D 53/047
95/99

(Continued)

FOREIGN PATENT DOCUMENTS

| GB | 345234 A | * 3/1931 | ............. C21B 13/08 |
|---|---|---|---|
| JP | 5406208 B2 | 2/2014 | |

(Continued)

OTHER PUBLICATIONS

Gan, M. et al. "Gasification Reaction Characteristics between Biochar and CO2 as well as the Influence on Sintering Process" Published Oct. 23, 2017 (Year: 2017).*

(Continued)

*Primary Examiner* — Medhanit W Bahta
(74) *Attorney, Agent, or Firm* — The Webb Law Firm

(57) ABSTRACT

The method for recycling carbon dioxide according to the present invention includes: injecting a reaction gas containing carbon dioxide and a carbon raw material into a rotary heating furnace; reacting the reaction gas and the carbon raw material with each other in the rotary heating furnace to generate a hydrocarbon precursor containing carbon monoxide; and converting the hydrocarbon precursor into a hydrocarbon compound, thereby exhibiting excellent conversion rate of carbon dioxide.

17 Claims, 2 Drawing Sheets

(51) Int. Cl.
  *C01B 13/32*   (2006.01)
  *F27B 7/10*   (2006.01)
  *F27B 7/20*   (2006.01)
  *B01J 19/28*   (2006.01)
  *C07C 41/01*   (2006.01)
  *C07C 29/151*   (2006.01)

(56) References Cited

U.S. PATENT DOCUMENTS 7,932,298 B2   4/2011  Young
8,911,520 B2   12/2014 Moller

FOREIGN PATENT DOCUMENTS

| KR | 100709268 B1 | 4/2007 |
| KR | 101100361 B1 | 12/2011 |
| KR | 101342226 B1 | 12/2013 |
| KR | 101440549 B1 | 9/2014 |

OTHER PUBLICATIONS

Nabertherm (Laboratory—Cole-Parmer, Published Oct. 24, 2016) (Year: 2016).*
Poudel, J. et al. "Process Design Characteristics of Syngas (CO/H2) Separation Using Composite Membrane" Sustainability 2019, 11, 703, Published Jan. 29, 2019 (Year: 2019).*

* cited by examiner

METHOD FOR RECYCLING CARBON DIOXIDE

CROSS-REFERENCE TO RELATED APPLICATION

This application claims priority to Korean Patent Application No. 10-2019-0041781 filed Apr. 10, 2019, the disclosure of which is hereby incorporated by reference in its entirety.

BACKGROUND OF THE INVENTION

1. Field of the Invention

The present invention relates to a method for recycling carbon dioxide, and more specifically, to a method for recycling carbon dioxide using a carbon raw material.

2. Description of the Related Art

Recently, due to global warming caused by environmental pollution, sea level rise and abnormal climate phenomenon are occurring. The main cause of the global warming is release of a large amount of carbon dioxide and the like. Therefore, a reducing the carbon dioxide has become an issue.

For example, a method for adhering or absorbing the released carbon dioxide to remove it into a deep sea, a method for storing the liquefied carbon dioxide in a ground surface layer, and the like are studied.

However, these methods are only to store the already formed carbon dioxide in a specific place, and there is a limitation in terms of storage places and the like. In addition, the above methods are only a means to temporarily prevent an increase in the amount of carbon dioxide present in the atmosphere, and cannot be a fundamental solution for removing the formed carbon dioxide. Accordingly, a necessity to develop a method for removing the carbon dioxide by converting it into a useful material has been increased.

For example, Korean Patent Registration No. 10-1100361 discloses a system for fixation of carbon dioxide using microalgae, however, has not proposed a method for converting the carbon dioxide into a useful material.

PRIOR ART DOCUMENT

Patent Document (Patent Document 1) Korean Patent Registration Publication No. 10-0709268 (May 4, 2006)

SUMMARY OF THE INVENTION

One object of the present invention is to provide a method for recycling carbon dioxide with high efficiency.

To achieve the above object, according to an aspect of the present invention, there is provided a method for recycling carbon dioxide including: injecting a reaction gas containing carbon dioxide and a carbon raw material into a rotary heating furnace; reacting the reaction gas and the carbon raw material in the rotary heating furnace to produce a hydrocarbon precursor containing carbon monoxide; and converting the hydrocarbon precursor into a hydrocarbon compound.

In exemplary embodiments, in the injecting the reaction gas and the carbon raw material, the carbon raw material may be injected into a front section in a length direction of the rotary heating furnace, and the reaction gas may be injected into a rear section in the length direction of the rotary heating furnace.

In exemplary embodiments, in the injecting the reaction gas and the carbon raw material, the reaction gas and the carbon raw material may be injected together into a front section in a length direction of the rotary heating furnace.

In exemplary embodiments, the reaction gas may be injected so that a retention time inside the rotary heating furnace is 10 to 60 minutes, and a ratio of an injection rate of the carbon raw material to an injection rate of the reaction gas is 2 to 5.

In exemplary embodiments, the carbon raw material may include coke, carbon black or graphite.

In exemplary embodiments, a reaction temperature in the rotary heating furnace may be 900 to 1,200° C.

In exemplary embodiments, a reaction pressure in the rotary heating furnace may be 0.1 to 10 bar.

In exemplary embodiments, the producing the hydrocarbon precursor may include rotating the rotary heating furnace by an axis in a length direction, while moving the carbon raw material and the reaction gas in the length direction of the rotary heating furnace.

In exemplary embodiments, a rotational speed of the rotary heating furnace may be 0.5 to 30 rpm.

In exemplary embodiments, a ratio of an inner length relative to an inner diameter of the rotary heating furnace may be 5 to 30.

In exemplary embodiments, the rotary heating furnace may be inclined by a predetermined slope ratio so that a front section in a length direction is higher than a rear section in the length direction.

In exemplary embodiments, the slope ratio may be 1 to 10%.

In exemplary embodiments, the rotary heating furnace may include a heating unit configured to directly heat the rotary heating furnace.

In exemplary embodiments, the producing the hydrocarbon precursor may include reacting carbon dioxide self-generated in the heating unit with the carbon raw material.

In exemplary embodiments, the method may further include removing nitrogen and water vapor from the hydrocarbon precursor before the converting the hydrocarbon precursor into the hydrocarbon compound.

In exemplary embodiments, the converting the hydrocarbon precursor into the hydrocarbon compound may include reacting the hydrocarbon precursor with a metal catalyst.

In exemplary embodiments, the metal catalyst may include iron oxide.

In exemplary embodiments, the converting the hydrocarbon precursor into the hydrocarbon compound may include reacting carbon monoxide with hydrogen to be converted into hydrocarbon.

In the method for recycling carbon dioxide according to exemplary embodiments of the present invention, the reaction gas containing carbon dioxide and the carbon raw material react with each other in the rotary heating furnace, and thus a conversion rate of carbon dioxide may be improved by appropriately adjusting a rotation speed, an inner length, and the like of the rotary heating furnace.

In some embodiments, an injection direction of the reaction gas and the carbon raw material into the rotary heating furnace may be appropriately adjusted for increasing reaction time and a contact time between the reaction gas and the carbon raw material, and thus the conversion rate of carbon dioxide may be improved.

In some embodiments, the rotary heating furnace includes the heating unit configured to directly heat the rotary heating furnace, and the carbon dioxide self-generated in the rotary heating furnace by the heating unit may react with the carbon raw material, and thus an additional generation of the carbon dioxide in a process of maintaining the rotary heating furnace at a high temperature may be prevented.

In some embodiments, the hydrocarbon precursor containing carbon monoxide collected from the rotary heating furnace may convert into a hydrocarbon compound, and thus the carbon dioxide may be effectively recycled.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

In embodiments of the present invention, a reaction gas containing carbon dioxide and a carbon raw material are injected into a rotary heating furnace. The injected reaction gas and the carbon raw material react with each other in the rotary heating furnace to generate a hydrocarbon precursor containing carbon monoxide. Then, the hydrocarbon precursor is converted into a hydrocarbon compound. Therefore, a conversion rate of carbon dioxide is improved, and a generation of additional carbon dioxide may be effectively prevented.

Hereinafter, embodiments of the present invention will be described in detail with reference to the accompanying drawings. However, these are merely an example, and the present invention is not limited to the specific exemplary embodiments.

As used herein, the term "hydrocarbon precursor" refers to a gas containing carbon monoxide generated by reacting a reaction gas containing carbon dioxide and a carbon raw material. The hydrocarbon precursor comprehensively refers to a gas containing carbon monoxide collected from the rotary heating furnace and converted into a hydrocarbon compound.

Figure 1:
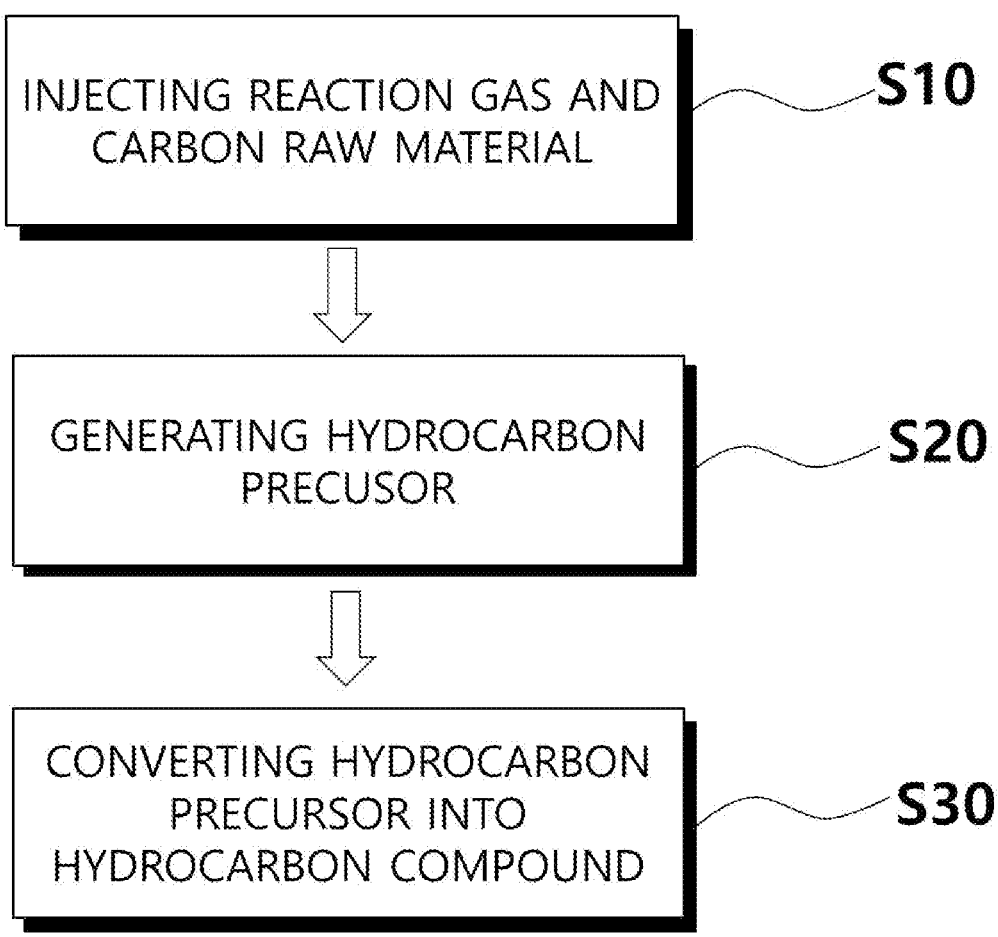
FIG. 1 is a flow chart illustrating a process of a method for recycling carbon dioxide according to exemplary embodiments of the present invention.
Figure 2:
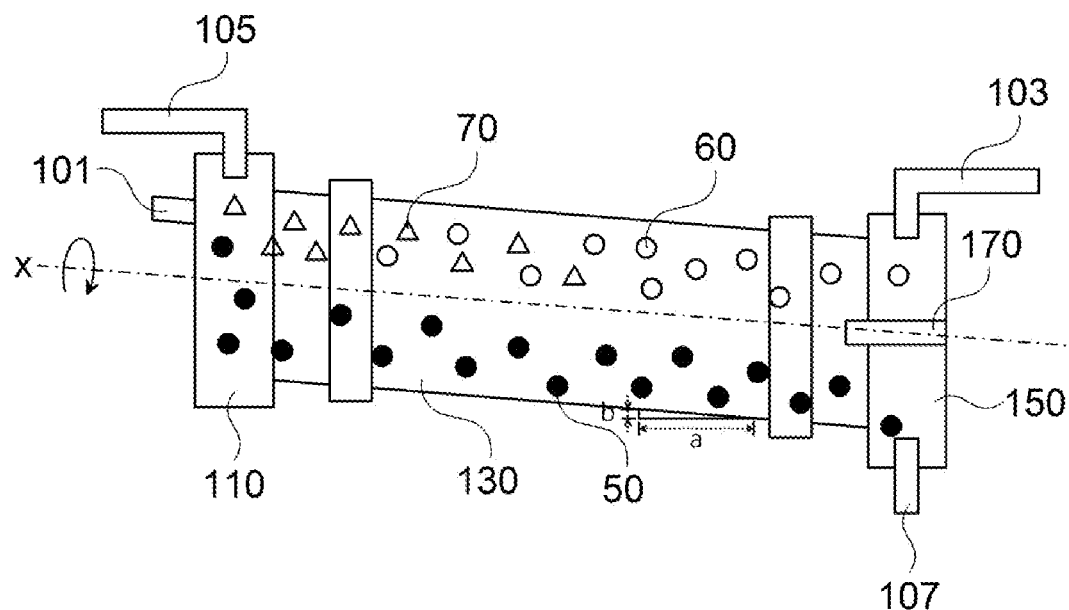
FIGS. 2 and 3 are schematic views illustrating rotary heating furnaces according to exemplary embodiments of the present invention.
Figure 3:
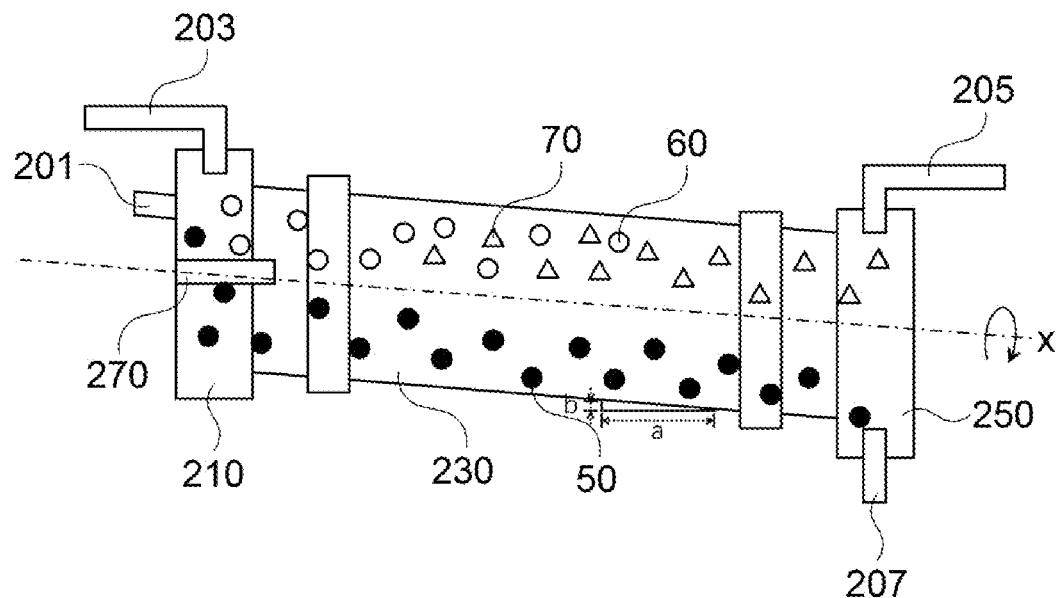

FIG. 1 is a flow chart illustrating processes of a method for recycling carbon dioxide according to exemplary embodiments of the present invention, and FIGS. 2 and 3 are schematic views illustrating rotary heating furnaces according to exemplary embodiments of the present invention.

Hereinafter, the method for recycling carbon dioxide according to embodiments of the present invention will be described in more detail with reference to FIGS. 1 to 3.

Referring to FIGS. 1 to 3, a carbon raw material 50 and a reaction gas 60 containing carbon dioxide may be injected into rotary heating furnaces 100 and 200 (for example, S10 process).

For example, the carbon raw material 50 may be injected into the rotary heating furnaces 100 and 200 through carbon raw material inlet ports 101 and 201, and the reaction gas 60 may be injected into the rotary heating furnaces 100 and 200 through reaction gas inlet ports 103 and 203.

Herein, the carbon raw material inlet ports 101 and 201 are not particularly limited in terms of a size and a position thereof, so long as the solid carbon raw material 50 can be easily injected into the rotary heating furnaces 100 and 200 therethrough. For example, the carbon raw material inlet ports 101 and 201 may be located at upper portions of the rotary heating furnaces 100 and 200 so as to facilitate an injection of the carbon raw material in a solid state.

In addition, the reaction gas inlet ports 103 and 203 are not particularly limited in terms of the size and the position, so long as the reaction gas 60 in a gaseous state can be easily injected into the rotary heating furnaces 100 and 200 therethrough. For example, the reaction gas inlet ports 101 and 201 may be located at upper portions of the rotary heating furnaces 100 and 200 so as to uniformly inject the carbon dioxide having a density higher than air into the rotary heating furnaces 100 and 200.

Referring to FIG. 2, the carbon raw material 50 may be injected into a front section 110 in a length direction of the rotary heating furnace 100, and the reaction gas 60 containing carbon dioxide may be injected into a rear section 150 in the length direction of the rotary heating furnace 100.

For example, the carbon raw material 50 may be injected into the front section 110 of the rotary heating furnace 100 through the carbon raw material inlet port 101 located in the front section 110 of the rotary heating furnace 100, and the reaction gas 60 may be injected into the rear section 150 of the rotary heating furnace 100 through the reaction gas inlet port 103 located in the rear section 150 of the rotary heating furnace 100.

For example, the carbon raw material 50 injected into the front section 110 may pass through a body 130 of the rotary heating furnace 100 to move to the rear section 150, and the reaction gas 60 injected into the rear section 150 may pass through the body 130 to move to the front section 110. Therefore, a counter flow of the carbon raw material 50 and the reaction gas 60 may be formed in the rotary heating furnace 100.

A contact area, a contact time, and a reaction time between the carbon raw material 50 in a solid state (e.g., solid carbon raw material 50) and the reaction gas 60 in a gaseous state (e.g., reaction gas 60) may be increased by the counter flow, and thus the conversion rate of carbon dioxide may be improved.

In addition, in a conventional rotary heating furnace, a solid and a gas react with each other therein to form a solid product. However, in the rotary heating furnace 100 of the present invention, a solid (for example, a carbon raw material) and a gas (for example, a reaction gas) react with each other therein to form a gaseous product (for example, the hydrocarbon precursor). Therefore, the product is not accumulated in the rotary heating furnace 100, but may move in the length direction of the rotary heating furnace 100. The solid carbon raw material 50 and the reaction gas 60 move in directions opposite to each other, and thus the reaction gas 60 may come into gradually contact with the carbon raw material 50 having high carbon content.

Therefore, an equilibrium in a production reaction of the hydrocarbon precursor containing carbon monoxide may be shifted toward the product, which will be described below, thus to increase a ratio of carbon dioxide converted into carbon monoxide among the carbon dioxides contained in the reaction gas 60.

In some embodiments, referring to FIG. 3, the carbon raw material 50 and the reaction gas 60 containing carbon dioxide may be injected together into the front section 210 in the length direction of the rotary heating furnace 200.

For example, the carbon raw material 50 may be injected into the front section 210 through the carbon raw material inlet port 201 located in the front section 210 of the rotary heating furnace 200, and the reaction gas 60 may be injected into the front section 210 through the reaction gas inlet port 203 located in the front section 210 of the rotary heating furnace 200.

For example, the carbon raw material 50 and the reaction gas 60, which are injected into the front section 210, may pass through the body 130 to move to the rear section 150. Thereby, a co-flow of the carbon raw material 50 and the reaction gas 60 may be formed in the rotary heating furnace 100.

Accordingly, a contact time during a reaction between the solid carbon raw material 50 and the reaction gas 60 which react with each other to generate the hydrocarbon precursor 70 containing carbon monoxide of a gas is increased, such that the conversion rate of carbon dioxide may be improved.

According to some embodiments, the reaction gas 60 may be injected so that a retention time in the rotary heating furnace 100 is about 10 to 60 minutes, and a ratio of an injection rate (g/hr) of the carbon raw material 50 to an injection rate (g/hr) of the reaction gas 60 may be about 2 to 5. Within the above-described range, the contact time and the contact area between the carbon raw material 50 and the reaction gas 60 may be increased, and thus the conversion rate of carbon dioxide may be further improved.

The retention time may refer to a time required for the reaction gas 60 injected into one end of the rotary heating furnace 100 to flow out from the other end of the rotary heating furnace 100.

Referring to FIGS. 1 to 3, the carbon raw material 50 and the reaction gas 60 may react with each other in the rotary heating furnaces 100 and 200 to generate the hydrocarbon precursor 70 containing carbon monoxide (for example, S20 process).

For example, carbon dioxide contained in the reaction gas 60 and carbon contained in the carbon raw material 50 may react with each other inside the rotary heating furnaces 100 and 200 as shown in Reaction Scheme 1 below to generate the hydrocarbon precursor 70 containing carbon monoxide.

   [Reaction Scheme 1]

For example, the reaction gas 60 and the carbon raw material 50 react with each other in the bodies 130 and 230 of the rotary heating furnaces 100 and 200 to produce the hydrocarbon precursor 70 containing carbon monoxide.

In this case, a type of the reaction gas 60 is not particularly limited so long as containing carbon dioxide, and an exhaust gas containing carbon dioxide emitted from various factories, means of transport, buildings, and the like may be used without a limitation thereof.

In some embodiments, the carbon raw material 50 may include coke, carbon black or graphite. For example, a content of carbon in the carbon raw material 50 may be about 80% or more, and preferably about 95% or more.

In some embodiments, a reaction temperature in the rotary heating furnaces 100 and 200 may be about 900 to 1,200° C. Within the above-described temperature range, the equilibrium of Reaction Scheme 1 may be shifted toward carbon monoxide, such that an amount of carbon dioxide converted into carbon monoxide may be increased.

In some embodiments, a reaction pressure in the rotary heating furnaces 100 and 200 may be about 0.1 to 10 bar. Within the above-described pressure range, the number of times the reaction gases 60 effectively collide with the carbon raw materials 50 is increased, such that the conversion rate of carbon dioxide converted into carbon monoxide may be increased.

In some embodiments, the rotary heating furnaces 100 and 200 may rotate about an axis (X) of the length direction of the rotary heating furnaces 100 and 200, respectively, while moving the carbon raw material 50 and the reaction gas 60 in the length direction thereof.

For example, the carbon raw material 50, which is a solid located at lower portions of the rotary heating furnaces 100 and 200, may move upward along sides of the rotary heating furnaces 100 and 200 as the rotary heating furnaces 100 and 200 rotate.

Accordingly, a mixture between the reaction gas 60 and the carbon raw material 50 is promoted, such that the contact area and the contact time between the reaction gas 60 and the solid carbon raw material 50 may be increased. For example, as the contact area and the contact time between the carbon raw material 50 and the reaction gas 60 are increased, a ratio of carbon dioxide converted into carbon monoxide among the carbon dioxides contained in the reaction gas 60 may be increased.

In some embodiments, a rotational speed of the rotary heating furnaces 100 and 200 may be about 0.5 to 30 rpm. For example, within the above-described rotational speed range, the contact area and the contact time between the reaction gas 60 and the carbon raw material 50 may be further increased, and thus the conversion rate of carbon dioxide may be further improved.

In some embodiments, a ratio of an inner length to an inner diameter of the rotary heating furnace 100 or 200 may be about 5 to 30. As used herein, the inner diameter may mean an internal diameter of a circle in which the rotary heating furnace 100 or 200 having a cylindrical shape is cut perpendicular to the length axis X, and the inner length may mean an internal distance in the length direction of the rotary heating furnace 100 or 200 having a cylindrical shape.

For example, within the above-described range of the ratio of the inner length to the inner diameter, the reaction time between the reaction gas 60 and the carbon raw material 50 may be increased, and the reaction gas 60 and the carbon raw material 50 may be more easily mixed. Therefore, the conversion rate of carbon dioxide contained in the reaction gas 60 may be further improved.

Herein, if the ratio of the inner length to the inner diameter of the rotary heating furnace 100 or 200 is less than about 5, the reaction time may be not sufficiently secured, thereby causing a reduction in the conversion rate of carbon dioxide.

In addition, if the ratio of the inner length to the inner diameter of the rotary heating furnace 100 or 200 exceeds about 30, the reaction time may be excessively increased, thereby causing a reduction in the conversion rate of carbon dioxide.

In some embodiments, two or more rotary heating furnaces 100 and 200 is connected in series such that the ratio of the inner length relative to the inner diameter satisfying the above range, and thus the conveniences of manufacture and operation of the rotary heating furnaces 100 and 200 and the conversion rate of carbon dioxide may be further improved.

In some embodiments, referring to FIGS. 2 and 3, the rotary heating furnaces 100 and 200 may be inclined by predetermined slope ratio(b/a*100) so that the front sections 110 and 210 in the length direction are higher than the rear sections 150 and 250 in the length direction. Seeing FIGS. 2 and 3, the slope ratio refers to percent ratio of "a" relative to "b".

For example, the rotary heating furnaces 100 and 200 inclined by predetermined slope ratio, includes the carbon raw material inlet ports 101 and 201 and outlet ports 107 and 207. The carbon raw material inlet ports 101 and 201 may be located in the front sections 110 and 210 of the rotary heating furnaces 100 and 200, and outlet ports 107 and 207 may be located in the rear sections 150 and 250 of the rotary heating furnaces 100 and 200.

For example, the carbon raw material inlet ports 101 and 201 may be located at the upper portions of the rotary heating furnaces 100 and 200, and the outlet ports 107 and 207 may be located at the lower portions of the rotary heating furnaces 100 and 200.

Accordingly, the carbon raw material 50, which is a solid state injected through the carbon raw material inlet ports 101 and 201, may easily move to the rear sections 150 and 250 of the rotary heating furnaces 100 and 200 along the predetermined slope ratio.

In addition, the carbon raw material 50, which is a solid injected into the rotary heating furnaces 100 and 200, may easily move in the length direction by gravity along the predetermined slope ratio.

For example, the carbon raw material 50 moves in the length direction along the predetermined slope ratio to react with the reaction gas 60, and the reacted carbon raw material 50 may be discharged through the outlet ports 107 and 207 located in the rear sections 150 and 250 of the rotary heating furnaces 100 and 200.

Therefore, the carbon raw material 50 having a reduced carbon concentration by reacting with the carbon dioxide may be easily removed, and the efficiency of the carbon dioxide recycling process may be improved by the carbon raw material 50 having a high concentration newly injected into the rotary heating furnaces 100 and 200.

In some embodiments, the slope ratio(b/a*100) may be about 1 to 10%. Within the above-described range, a moving speed of the carbon raw material 50 which moves from the front sections 110 and 210 to the rear sections 150 and 250 of the rotary heating furnaces 100 and 200 may be most appropriate. Therefore, the contact time between the carbon raw material 50 and the reaction gas 60 may be increased, thus to further improve the conversion rate of carbon dioxide.

For example, the hydrocarbon precursor 70 containing carbon monoxide produced by the reaction between the carbon raw material 50 and the reaction gas 60 may be collected through recovery ports 105 and 205.

For example, the positions of the recovery ports 105 and 205 are not particularly limited, and the recovery ports may be located at the upper portions of the rotary heating furnaces 100 and 200 to more easily collect the hydrocarbon precursor containing carbon monoxide having a density lower than air.

Referring to FIG. 2, the recovery port 105 may be located in the front section 110 of the rotary heating furnace 100, and the reaction gas inlet port 103 may be located in the rear section 150 of the rotary heating furnace 100.

Therefore, the reaction gas 60 injected into the rear section 150 may react with the carbon raw material 50 in the body 130 to generate the hydrocarbon precursor 70 containing carbon monoxide. The generated hydrocarbon precursor 70 may move from the body 130 to the front section 110 to be collected through the recovery port 105.

Referring to FIG. 3, the reaction gas inlet port 203 may be located in the front section 210 of the rotary heating furnace 200, and the recovery port 205 may be located in the rear section 250 of the rotary heating furnace 200.

Therefore, the reaction gas 60 injected into the front section 210 may react with the carbon raw material 50 in the body 230 to generate the hydrocarbon precursor 70 containing carbon monoxide. The generated hydrocarbon precursor 70 may move from the body 230 to the rear section 250 to be collected through the recovery port 105 located in the rear section 250.

According to some embodiments, heating units 170 and 270 for directly heating the rotary heating furnaces 100 and 200 may be located inside the rotary heating furnaces 100 and 200. For example, the rotary heating furnaces 100 and 200 may be direct firing rotary kilns.

For example, the heating units 170 and 270 may be located in the rotary heating furnaces 100 and 200 to maintain the temperature in the direct rotary heating furnaces 100 and 200 within the above-described reaction temperature range.

For example, the heating units 170 and 270 may be used without limitation so long as they can directly heat the insides of the rotary heating furnaces 100 and 200 to maintain the temperatures in the rotary heating furnaces 100 and 200 within the above-described reaction temperature range.

For example, the heating unit 170 may be a burner or heater that burns a fuel to maintain the temperatures in the rotary heating furnaces 100 and 200 within the above-described reaction temperature range.

According to some embodiments, the carbon dioxide 50 self-generated in the heating units 170 and 270 may react with the carbon raw material 50 to generate the hydrocarbon precursor 70 containing carbon monoxide. Therefore, the carbon dioxide additionally generated in the carbon dioxide recycling process may be effectively removed.

For example, referring to FIG. 2, the heating unit 170 may be disposed in the rear section 150. On the other hand, referring to FIG. 3, the heating unit 270 may be disposed in the front section 210.

For example, referring to FIGS. 2 and 3, the heating units 170 and 270 may be located at the same location where the reaction gas inlet ports 103 and 203 are located.

For example, when the reaction gas inlet port 103 is located in the rear section 150, the heating unit 170 may also be located in the rear section 150, and when the reaction gas inlet port 203 is located in the front section 210, the heating unit 270 may also be located in the front section 210. Therefore, the carbon dioxide additionally generated in the carbon dioxide recycling process may be effectively removed.

As described above, by adjusting the length, rotation speed, reaction temperature, reaction pressure, slope ratio, injection direction and injection speed of the rotary heating furnace 100 or 200, an efficiency of the reaction between the reaction gas 60 and the carbon raw material 50 may be increased to improve the conversion rate of carbon dioxide.

For example, the conversion rate of carbon dioxide may be 95% or more, and preferably 99% or more. In addition, the content of carbon monoxide contained in the hydrocarbon precursor 70 may be 85% by weight or more, and preferably 90% by weight or more.

According to exemplary embodiments, the hydrocarbon precursor containing the carbon monoxide may be converted into a hydrocarbon compound (for example, step S30).

For example, the hydrocarbon compound may include an alcohol compound, an ether compound, or a saturated hydrocarbon compound.

For example, the hydrocarbon precursor 70 may be converted into a hydrocarbon compound according to Reaction Scheme 2 below. For example, carbon monoxide included in the hydrocarbon precursor 70 may be converted into a hydrocarbon compound by reacting with hydrogen according to Reaction Scheme 2 below. For example, the conversion rate of carbon monoxide may be about 60% or more.

$$nCO+(4n+2)H_2 \rightarrow C_nH_{2n+2}+nH_2O \quad \text{[Reaction Scheme 2]}$$

In Reaction Scheme 2, n may be an integer of 1 or more.

For example, the hydrocarbon precursor 70 may be converted into a hydrocarbon compound including an alcohol compound or an ether compound according to Reaction Schemes 3 and 4 below.

$$2CO+6H_2 \rightarrow 2CH_3OH+H_2O \quad \text{[Reaction Scheme 3]}$$

$$2CH_3OH \rightarrow CH_3OCH_3+H_2O \quad \text{[Reaction Scheme 4]}$$

Therefore, the carbon dioxide may be easily converted into the hydrocarbon compound having high availability.

According to exemplary embodiments, nitrogen and water vapor may be removed from the generated hydrocarbon precursor 70 before converting the hydrocarbon precursor 70 into the hydrocarbon compound.

For example, the water vapor and nitrogen included in the hydrocarbon precursor 70 may be derived from air included in the reaction process of the carbon raw material 50 and reaction gas 60.

For example, the water vapor or nitrogen contained in the hydrocarbon precursor 70 may react with hydrogen to reduce a productivity of the hydrocarbon compound. Therefore, by removing the nitrogen and water vapor from the hydrocarbon precursor 70, the productivity of the hydrocarbon compound may be improved.

For example, the hydrocarbon precursor 70 may react with hydrogen at a temperature of about 150 to 350° C. to generate a hydrocarbon compound. For example, a production rate of the hydrocarbon compound within the above-described temperature range may be improved.

According to exemplary embodiments, the hydrocarbon precursor 70 may react with hydrogen at a pressure of about 5 to 15 bar to be converted into a hydrocarbon compound. For example, within the above-described pressure range, the equilibrium of the reaction may be shifted to a direction in which the hydrocarbon precursor is converted into a hydrocarbon compound, such that the production rate of the hydrocarbon compound may be improved.

According to exemplary embodiments, the hydrocarbon precursor may react with a metal catalyst to be converted into the hydrocarbon compound.

For example, the metal catalyst may include at least one selected from the group consisting of cobalt, iron, or ruthenium. Preferably, the metal catalyst may include iron oxide.

Therefore, the production rate of hydrocarbons may be increased, such that economic advantages and productivity in a regeneration process of carbon dioxide may be further improved.

According to exemplary embodiments, carbon monoxide may react with hydrogen to be converted into a hydrocarbon. For example, carbon monoxide generated by reaction between the carbon dioxide and the carbon raw material may be converted into hydrocarbons having various availabilities. Therefore, the recycling efficiency of carbon dioxide may be improved.

Hereinafter, preferred examples are proposed to more concretely describe the present invention. However, the following examples are only given for illustrating the present invention and those skilled in the art will obviously understand that various alterations and modifications are possible within the scope and spirit of the present invention. Such alterations and modifications are duly included in the appended claims.

EXPERIMENTAL EXAMPLE

Example 1

A cylindrical rotary heating furnace having an inner diameter of 15 cm, an outer diameter of 17 cm, and an inner length of 100 cm was prepared. The rotary heating furnace was inclined at a slope angle(b/a*100) of 5%. A retention time of carbon dioxide injected into a rear section of the rotary heating furnace was 30 minutes, and an injection rate was 50 g/h. The injection rate of coke (with a carbon content of 80%) injected into a front section of the rotary heating furnace was 113 g/hr, and a ratio of the injection rate of coke to the injection rate of carbon dioxide was 2.26.

A temperature and a pressure in the rotary heating furnace were adjusted to 1000° C. and 3 bar, respectively. Then, the carbon dioxide and the coke reacted to generate carbon monoxide, while rotating the rotary heating furnace at a rotation speed of 5 rpm.

Concentrations of carbon dioxide before and after the reaction were measured to calculate a conversion rate of carbon dioxide converted into carbon monoxide. The calculated conversion rate is listed in Table 1 below.

Examples 2 to 7

The conversion rates of carbon dioxide were calculated in the same manner as Example 1, except that the rotation speed of the rotary heating furnace, the injection rate of coke, the injection rate of carbon dioxide, and the length of the rotary heating furnace were changed as listed in Table 1 below.

COMPARATIVE EXAMPLE 1

Coke and carbon dioxide were injected into a batch type closed reactor. The temperature and pressure in the reactor were adjusted to 1000° C. and 3 bar, respectively, and a reaction between carbon dioxide and coke was executed to produce carbon monoxide.

Concentrations of carbon dioxide before and after the reaction were measured to calculate conversion rates of carbon dioxide converted into carbon monoxide. The calculated conversion rates are listed in Table 1 below.

TABLE 1

|  | Temperature (° C.) | Pressure (bar) | Rotation speed (RPM) | Ratio of inner length to inner diameter of rotary heating furnace | Slope angle of rotary heating furnace (%) | Conversion rate (%) of $CO_2$ |
|---|---|---|---|---|---|---|
| Example 1 | 1000 | 3 | 5 | 6.7 | 5 | 99 |
| Example 2 | 1000 | 3 | 0.3 | 6.7 | 5 | 92 |

TABLE 1-continued

|  | Temperature (° C.) | Pressure (bar) | Rotation speed (RPM) | Ratio of inner length to inner diameter of rotary heating furnace | Slope angle of rotary heating furnace (%) | Conversion rate (%) of $CO_2$ |
|---|---|---|---|---|---|---|
| Example 3 | 1000 | 3 | 6 | 6.7 | 5 | 98 |
| Example 4 | 1000 | 3 | 5 | 3 | 5 | 90 |
| Example 5 | 1000 | 3 | 5 | 40 | 5 | 96 |
| Example 6 | 1000 | 3 | 5 | 6.7 | 2 | 98 |
| Example 7 | 1000 | 3 | 5 | 6.7 | 12 | 91 |
| Comparative Example 1 | 1000 | 3 | — | — | — | 70 |

Referring to the above Table 1, it can be confirmed that the examples in which carbon dioxide and coke reacted with each other using the rotary heating furnace have better conversion rates of carbon dioxide ($CO_2$) than the comparative example.

What is claimed is:

1. A method for recycling carbon dioxide comprising:
   injecting a reaction gas containing carbon dioxide and a carbon raw material into a rotary heating furnace;
   reacting the reaction gas and the carbon raw material with each other in the rotary heating furnace to generate a hydrocarbon precursor containing carbon monoxide; and
   converting the hydrocarbon precursor into a hydrocarbon compound,
   wherein the rotary heating furnace includes a heating unit configured to directly heat the rotary heating furnace, and
   a ratio of an injection rate of the carbon raw material in g/hr relative to an injection rate of the reaction gas in g/hr is from 2 to 5.

2. The method for recycling carbon dioxide according to claim 1, wherein, in the injecting the reaction gas and the carbon raw material, the carbon raw material is injected into a front section in a length direction of the rotary heating furnace, and the reaction gas is injected into a rear section in the length direction of the rotary heating furnace.

3. The method for recycling carbon dioxide according to claim 1, wherein, in the injecting the reaction gas and the carbon raw material, the reaction gas and the carbon raw material are injected together into a front section in a length direction of the rotary heating furnace.

4. The method for recycling carbon dioxide according to claim 1, wherein the reaction gas is injected so that a retention time in the rotary heating furnace is 10 to 60 minutes.

5. The method for recycling carbon dioxide according to claim 1, wherein the carbon raw material includes coke, carbon black or graphite.

6. The method for recycling carbon dioxide according to claim 1, wherein a reaction temperature in the rotary heating furnace is 900 to 1,200° C.

7. The method for recycling carbon dioxide according to claim 1, wherein a reaction pressure in the rotary heating furnace is 0.1 to 10 bar.

8. The method for recycling carbon dioxide according to claim 1, wherein the producing the hydrocarbon precursor includes rotating the rotary heating furnace by an axis in a length direction, while moving the carbon raw material and the reaction gas in the length direction of the rotary heating furnace.

9. The method for recycling carbon dioxide according to claim 8, wherein a rotational speed of the rotary heating furnace is 0.5 to 30 rpm.

10. The method for recycling carbon dioxide according to claim 1, wherein a ratio of an inner length relative to an inner diameter of the rotary heating furnace is 5 to 30.

11. The method for recycling carbon dioxide according to claim 1, wherein the rotary heating furnace is inclined by a predetermined slope ratio so that a front section in a length direction is higher than a rear section in the length direction.

12. The method for recycling carbon dioxide according to claim 11, wherein the slope ratio is 1 to 10%.

13. The method for recycling carbon dioxide according to claim 1, wherein producing the hydrocarbon precursor included reacting carbon dioxide self-generated in the rotary heating furnace with the carbon raw material.

14. The method for recycling carbon dioxide according to claim 1, further including removing nitrogen and water vapor from the hydrocarbon precursor before converting the hydrocarbon precursor into the hydrocarbon compound.

15. The method for recycling carbon dioxide according to claim 1, wherein the converting the hydrocarbon precursor into the hydrocarbon compound includes reacting the hydrocarbon precursor with a metal catalyst.

16. The method for recycling carbon dioxide according to claim 15, wherein the metal catalyst includes iron oxide.

17. The method for recycling carbon dioxide according to claim 1, wherein the converting the hydrocarbon precursor into the hydrocarbon compound includes reacting carbon monoxide with hydrogen to be converted into hydrocarbon.

* * * * *